(12) United States Patent
Ban et al.

(10) Patent No.: US 8,404,448 B2
(45) Date of Patent: Mar. 26, 2013

(54) DNA APTAMER SPECIFICALLY BINDING TO HUMAN CARDIAC TROPONIN I

(75) Inventors: Changill Ban, Pohang-si (KR); Kyung-Mi Song, Pohang-si (KR); Weejeong Jeon, Daejeon (KR)

(73) Assignee: Postech Academy-Industry Foundation, Pohang-si, Gyeongsangbuk-do (KR)

( * ) Notice: Subject to any disclaimer, the term of this patent is extended or adjusted under 35 U.S.C. 154(b) by 0 days.

(21) Appl. No.: 13/355,234

(22) Filed: Jan. 20, 2012

(65) Prior Publication Data

US 2012/0316326 A1 Dec. 13, 2012

(30) Foreign Application Priority Data

Jun. 7, 2011 (KR) .................. 10-2011-0054795
Dec. 29, 2011 (KR) .................. 10-2011-0145434

(51) Int. Cl.
*C12Q 1/68* (2006.01)
(52) U.S. Cl. ..................................... 435/6.12
(58) Field of Classification Search .............. 435/198, 435/6.12
See application file for complete search history.

(56) References Cited

FOREIGN PATENT DOCUMENTS

| | | |
|---|---|---|
| GB | 2 200 358 A | 8/1988 |
| WO | 96/10076 A1 | 4/1996 |

OTHER PUBLICATIONS

Partial Search Report dated Sep. 21, 2012 of the corresponding European Patent Application No. 12151421.0—9 pages.
Database WPI Week 200781 Thomson Scientific, London, GB; AN 2007-873522 XP002681755 and CN 1 974 594 A (Inst Hygiene & Environmental Medicine MI), abstract, Jun. 16, 2010.
Database WPI Week 201050 Thomson Scientific, London, GB; AN 2010-J41788 XP002681756 and CN 101 738 425 A (Univ Tianjin Sci & Technology), abstract, Jun. 16, 2010.
Nandhikonda et al., "An Abiotic Fluorescent Prove for Cardiac Troponin I", Journal of the American Chemical Society, Jan. 1, 2011, vol. 133, pp. 14972-14974.
Christoph Maier, "Losliches CD40L als neuer Ligand des Leukozytenintegrins Mac-1 and seine Bedutung bei der Atherosklerose sowie methodische Untersuchungen zur Selektion eines Troponin T spezifischen Aptamers zur Myokardischamiediagnostik", Ph. D. thesis, Jan. 1, 2007, pp. I-V, 1-192, XP55033104, Freiburg, DE.
Collinson et al., "Measurement of cardiac troponins", Annals of Clinical Biochemistry, British Medical Association, London, GB, Jan. 1, 2001, vol. 38, pp. 423-449, XP009033233, ISSN: 0004-5632.
Liu et al., "Selection of aptamers against cardiac troponin I by SELEX", it in Medicine and Education (ITME), 2011 International Symposium on, IEEE, Dec. 9, 2011, pp. 536-539, XP032095661.

*Primary Examiner* — Tekchand Saidha
*Assistant Examiner* — Rama P Ramanujam
(74) *Attorney, Agent, or Firm* — Knobbe Martens Olson & Bear, LLP

(57) ABSTRACT

Disclosed are a DNA aptamer specifically binding to human cardiac troponin I, and a composition and a diagnostic kit for the diagnosis of acute cardiovascular diseases, comprising the same. Being superior in specificity and stability to antibodies which are conventionally used to diagnose acute cardiovascular diseases, the DNA aptamers specifically binding to human cardiac troponin I can be developed into biosensors which determine human cardiac troponin I levels with high sensitivity and accuracy, greatly contributing to the diagnosis in an early stage of acute cardiovascular diseases. It is expected to lots of help for increase of diagnostic accuracy.

3 Claims, 15 Drawing Sheets

Troponin T, I, C complex

SEQ ID NO: 3

SEQ ID NO: 4

SEQ ID NO: 2

SEQ ID NO: 3

DNA APTAMER SPECIFICALLY BINDING TO HUMAN CARDIAC TROPONIN I

CROSS-REFERENCE(S) TO RELATED APPLICATIONS

The present application claims priority of Korean Patent Application Nos. 10-2011-0054795 and 10-2011-0145434, filed on Jun. 7, 2011 and Dec. 29, 2011, respectively, which is incorporated herein by reference in its entirety.

BACKGROUND OF THE INVENTION

1. Field of the Invention

The present invention relates to a DNA aptamer specifically binding to human cardiac troponin I, and a composition and a diagnostic kit for the diagnosis of acute cardiovascular diseases, comprising the same.

2. Description of the Related Art

Troponin is a complex of three regulatory proteins (troponin C, troponin I and troponin T) that is attached to the protein tropomyosin and lies within the groove between actin filaments in muscle tissue to regulate the contraction and relaxation of muscle cells. When the intracellular levels thereof rise, $Ca^{2+}$ is bound to specific sites on Troponin C to produce a conformational change in Troponin I so that myosin can attach to the actin filament active sites, giving rise to the contraction of the muscle. This action is observed in both skeletal and cardiac muscles. The length of the amino acid sequence of Troponin I and Troponin T that act on cardiac muscle are different from the corresponding ones expressed in skeletal muscle.

The expression level of cardiac troponin I is known to rapidly increase upon the outbreak of acute cardiovascular diseases. Thus, the detection of this protein is very important for the initial diagnosis of acute cardiovascular diseases.

An aptamer is a single strand DNA (ssDNA) or RNA (ssRNA) that binds to a specific target. Thanks to their high affinity and stability to a specific target, they have recently been extensively developed and actively applied to the therapy and sensors for diagnosis of diseases. The synthesis of aptamers can be relatively simple, and cells, proteins and even small organic substance can be utilized as their targets, which allows for the development of new detection methods. In addition, aptamers find a wide range of applications in various fields, including the development of therapeutics, drug delivery systems, biosensors for diagnosis, etc. because their specificity and stability are superior to those of the antibodies that were developed previously.

Antibodies developed for diagnostic use are prepared using the immune system and thus suffer from the disadvantage of their preparation consuming a lot of time and expense, comparatively. Further, they are proteins that have poor stability, compared to aptamers, DNA or RNA, which may act as an obstruction to the development of highly sensible sensors.

Although many detection systems for troponin I have been developed on the basis of antibodies to troponin I, as mentioned above, they are subject to a lot of limitations. There is therefore a need for a detection system that is more stable and which can be operated at low cost and effectively diagnoses acute cardiovascular diseases in an early stage.

SUMMARY OF THE INVENTION

The present invention is to provide a DNA aptamer specifically binding to human cardiac troponin I, and a composition and a kit for the diagnosis of an acute cardiovascular disease, comprising the same.

However, the technical objects to be achieved by the present invention are not limited to those mentioned above and other objects may be clearly understood by those skilled in the art from the description given below.

In accordance with an aspect thereof, the present invention provides an aptamer that specifically binds to human cardiac troponin I which has a base sequence selected from the group consisting of SEQ ID NOS: 1 to 6.

In accordance with another aspect thereof, the present invention provides a composition for the diagnosis of an acute cardiovascular disease, comprising a DNA aptamer specifically binding to human cardiac troponin I.

In accordance with a further aspect thereof, the present invention provides a diagnostic kit for an acute cardiovascular disease that uses a DNA aptamer that specifically binds to human cardiac troponin I.

Superior in specificity and stability to antibodies which are conventionally used to diagnose acute cardiovascular diseases, the DNA aptamers specifically binding to human cardiac troponin I in accordance with the present invention can be developed into biosensors which determine human cardiac troponin I levels with sensitivity and accuracy, greatly contributing to the diagnosis in an early stage of acute cardiovascular diseases. It is expected to lots of help for increase of diagnostic accuracy.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
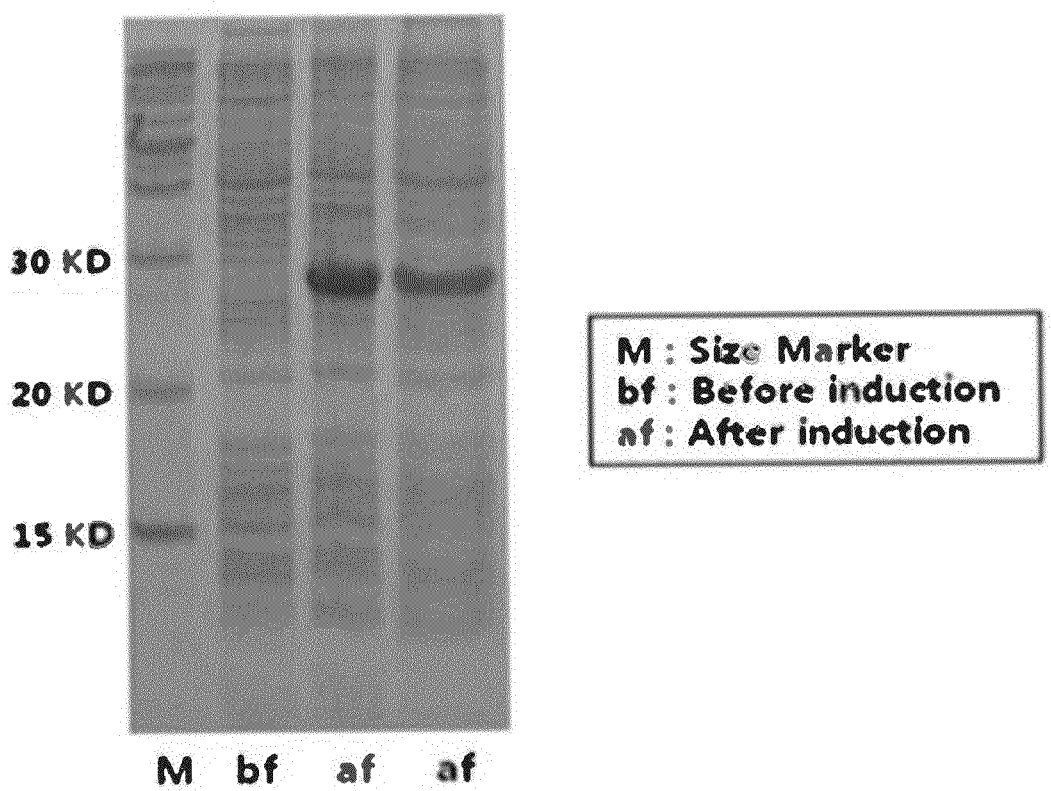
FIG. 1 shows the expression of Troponin I protein as measured by SDS PAGE.

To develop an aptamer as a substitute for an antibody to cardiac troponin I, human cardiac troponin I was expressed in a bacterial expression system, purified, and utilized to select DNA aptamers with the SELEX (Systematic Evolution of Ligands by EXponential enrichment) technique, which were then analyzed for sequence and structure, culminating in the present invention.

In greater detail, the present invention provides a DNA aptamer having the base sequence of one of SEQ ID NOS: 1 to 6 that specifically binds to human cardiac troponin I.

Also, the present invention provides a composition and a kit for the diagnosis of an acute cardiovascular disease, comprising a DNA aptamer specifically binding to human cardiac troponin I.

In addition to the DNA aptamer, the composition of the present invention may comprise pharmaceutically or physiologically acceptable vehicles, excipients or diluents.

Examples of the vehicles, excipients and diluents include lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinylpyrrolidone, water, methyl hydroxybenzoate, propylhydroxybenzoate, talc, magnesium stearate, and mineral oil. When formulated into dosage forms, the composition may further comprise typical filters, thickeners, binders, disintegrants, surfactants, anti-coagulants, lubricants, wetting agents, fragrant, emulsifiers, and/or preservatives.

A better understanding of the present invention may be obtained through the following examples which are set forth to illustrate, but are not to be construed as limiting the present invention.

EXAMPLE 1

Troponin I Gene Cloning

For use in the amplification of a human cardiac troponin I gene, a 5' primer with a BamH1 restriction site (GGATCC ATG GCGGAT GGG AGC AG; SEQ ID NO: 7) and a 3' primer with a Hind3 restriction site (AAGCTT TCAAAA CTT TTT CTT GCG G; SEQ ID NO: 8) were synthesized. For use in the amplification of a human cardiac troponin T gene, a 5' primer with a EcoRI restriction site (GAATTC ATG TCT GAC ATA GAA GAG GTG GTG; SEQ ID NO: 9) and a 3' primer with a XhoI restriction site (CTCGAG CTA TTT CCA GCG CCC GGT; SEQ ID NO: 10) were synthesized. And for use in the amplification of a human cardiac troponin C gene, a 5' primer with a EcoRI restriction site (GAATTC ATG GAT GAC ATC TAC AAG GCT GC; SEQ ID NO: 11) and a 3' primer with a XhoI restriction site (CTCGAG CTA CTC CAC ACC CTT CAT GAA CTC; SEQ ID NO: 12) were synthesized. Using these primers, amplification was conducted on the cDNA obtained from HEK293 cells in the presence of i-pfu polymerase. In this regard, PCR was performed with 30 cycles of 1) denaturing the double strand of the template at 95° C. for 1 min, 2) annealing the template with the primers at 58° C. for 30 sec, and 3) extending new strands at 72° C. for 1 min.

The amplified human cardiac troponin I gene and troponin C gene were digested with the restriction enzymes, ligated to a pET28a vector containing (His)6-tag. The amplified human cardiac troponin T gene was digested with the restriction enzymes, ligated to a pET21a vector. Troponin I gene and Troponin C gene were transformed into BL21(DE3) *E. coli*. For co-expression with troponin I, troponin T gene was transformed into BL21-CodonPlus (DE3)-RIG *E. coli*.

EXAMPLE 2

Expression of Troponin I Protein

The BL21(DE3) cells transformed with the human cardiac troponin I gene were grown at 37° C. in an LB (Luria Bertani) medium to an $OD_{600}$ (optical density) of 0.6. Subsequently, the expression of the protein was induced by incubating the cells at 18° C. for 16 hours in the presence of 0.2 mM IPTG (isopropyl-thio-β-D-galactopyranoside). The expression of the protein was confirmed by SDS-PAGE (sodium dodecyl sulfate polyacrylamide gel electrophoresis). After being harvested by centrifugation, the cells were washed once with PBS (10 mM sodium phosphate, 150 mM NaCl, pH 7.4). The SDS-PAGE results are shown in FIG. 1.

In FIG. 1, a marker (M) for indicating protein sizes was run on lane 1, the protein obtained before IPTG induction (bf) on lane 2, and proteins obtained after IPTG (af) on lanes 3 and 4. As can be seen in the SDS PAGE of FIG. 1, Troponin I, was detected at 28 KD after the IPTG induction.

EXAMPLE 3

Expression of Troponin Complex

As expression of troponin I, T, BL21-CodonPlus (DE3)-RIG *E. coli*, transformed with human cardiac troponin I gene and troponion T gene, and BL21(DE3) cell transformed with troponin C gene were grown at 37° C. in an LB (Luria Bertani) medium to an $OD_{600}$ (optical density) of 0.6. Subsequently, the expression of the protein was induced by incubating the cells at 18° C. for 16 hours in the presence of 0.2 mM IPTG (isopropyl-thio-β-D-galactopyranoside). The expression of the protein was confirmed by SDS-PAGE (sodium dodecyl sulfate polyacrylamide gel electrophoresis). After being harvested by centrifugation, the cells were washed once with PBS (10 mM sodium phosphate, 150 mM NaCl, pH 7.4). The SDS-PAGE results are shown in FIG. 2.

Figure 2:
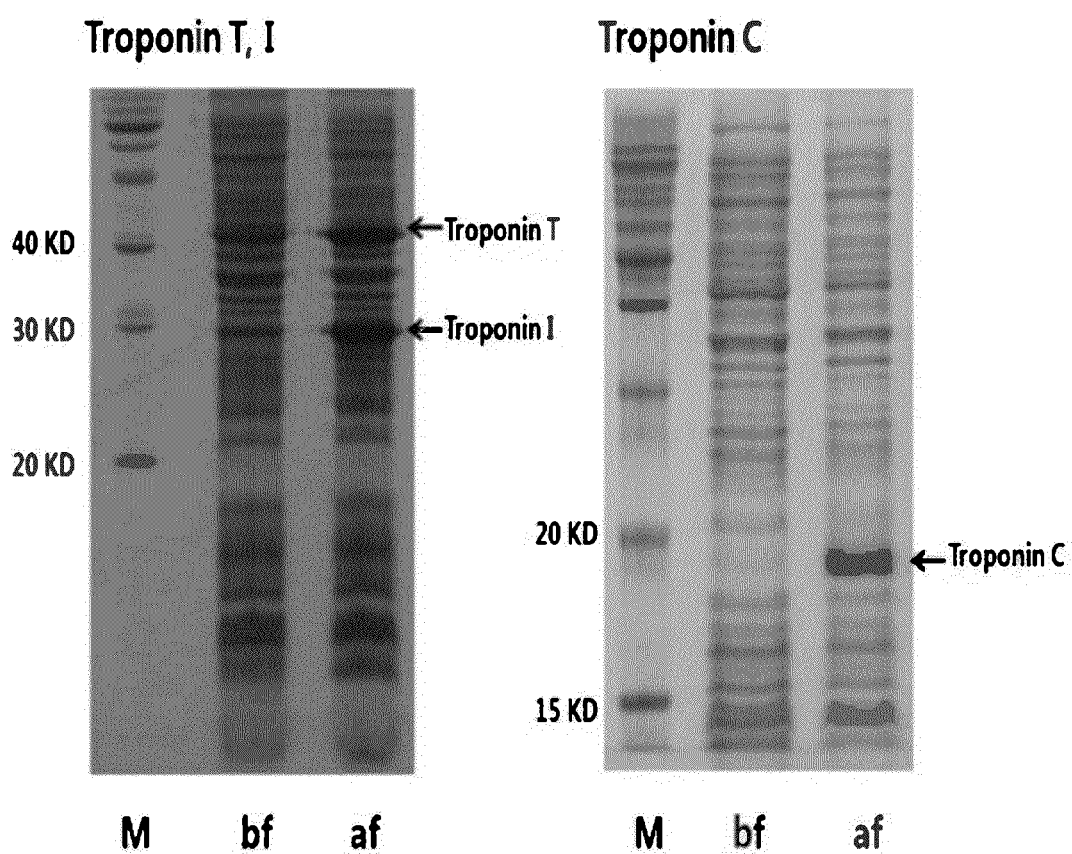
FIG. 2 shows the expression of Troponin complex protein as measured by SDS PAGE.

In FIG. 2, a marker (M) for indicating protein sizes was run on lane 1, the protein obtained before IPTG induction (bf) on lane 2. As can be seen in the SDS PAGE of FIG. 2, Troponin I, Troponin T and Troponin C were detected after the IPTG induction.

EXAMPLE 4

Purification of Troponin I Protein

To isolate the human cardiac troponin I protein expressed in the bacterial cell BL21(DE3) to a high purity, the cells were lysed in a lysis buffer (20 mM Tris, 500 mM NaCl, 0.5 mM β-mercaptoethanol, 3% glycerol, 0.01% Tween 20, pH 8.0) and ruptured by sonication for 10 min. Centrifugation at 15,000 rpm for 30 min separated proteins in a supernatant from the cell debris.

The affinity of Ni-NTA (Ni-Nitrilo-triacetic acid) for the (His)6-tag amino acid residues was used to isolate the protein to a high purity. In this regard, FPLC (Fast protein liquid chromatography) was coupled with an Ni-NTA column to which the supernatant containing cardiac troponin I was then loaded. The target protein bound to the column was eluted with elution buffer (20 mM Tris, 500 mM NaCl, 0.5 mM β-mercaptoethanol, 3% glycerol, 0.01% tween 20,300 mM imidazole, pH 8.0) because the (His)6-tag of the protein competes with imidazole.

For additional purification, the fraction containing cardiac troponin was subjected to size exclusion chromatography by gel filtration using a Superdex75 column to obtain more pure protein. The imidazole used was removed with the final buffer (20 mM Tris, 300 mM NaCl, 0.5 mM β-mercaptoethanol, 3% glycerol, 0.01% tween 20, pH 8.0). The results are shown in FIG. 3.

Figure 3:
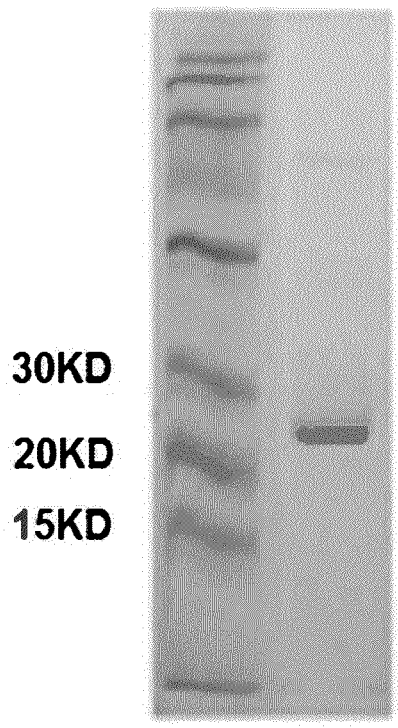
FIG. 3 shows the isolation of Troponin I protein as purified by gel filtration.

In FIG. 3, a marker for indicating protein sizes was run on lane 1 and the fraction obtained from the above-mentioned purification processes was on lane 2. As can be seen in the SDS-PAGE of FIG. 3, Troponin of high purity I was detected at 25 kD.

EXAMPLE 5

Purification of Troponin Complex (Troponin T, C, I)

To isolate the troponin complex protein to a high purity, the cells, were expressed troponin I and troponin T, were lysed in a lysis buffer (20 mM Tris, 500 mM NaCl, 0.5 mM β-mercaptoethanol, 5% glycerol, pH 8.0) and ruptured by sonication. And soluble proteins were isolated by Centrifugation.

As purification of troponin T and I proteins, the affinity of Ni-NTA (Ni-Nitrilo-triacetic acid) for the (His)6-tag amino acid residues was used to isolate the protein to a high purity. In this regard, FPLC (Fast protein liquid chromatography) was coupled with an Ni-NTA column to which the supernatant containing troponin T and troponin I was then loaded. The target protein bound to the column was eluted with elution buffer (20 mM Tris, 500 mM NaCl, 0.5 mM β-mercaptoethanol, 5% glycerol, 300 mM imidazole, pH 8.0).

For confirmation of troponin complex and measurement of SPR, troponin C with a (His)6-tag was made. (His)6-tag of troponin I and troponin T was eliminated by TEV (Tobacco Etch Virus) protease. Specifically, for recognition of TEV protease behind (His)6-tag and elimination, TEV protease and protein were performed at 20° C. for 6 hr.

Troponin I and troponin T were eluted by removing imidazole in elution buffer with G-25 column. And then loaded Ni-NTA column, Purified troponin I and troponin T were gotten by separating from (His)6-tag Troponin C was purified by Ni-NTA column with containing (His)6-tag and eluted from imidazole by G-25 column.

For getting of troponin complex, troponin C which contains purified (His)6-tag was coupled with Ni-NTA, loaded supernatant containing troponin T and troponin I, and then induced to formation of troponin complex.

Troponin I and troponin T which were not coupled with Troponin C were passed, troponin complex was gotten by elution buffer.

For additional purification, troponin complex was subjected to size exclusion chromatography by gel filtration using a Superdex 200 column to obtain more pure protein. The imidazole used was removed with the final buffer (20 mM Tris, 300 mM NaCl, 0.5 mM β-mercaptoethanol, 5% glycerol, pH 8.0). The results are shown in FIG. 4.

Figure 4:
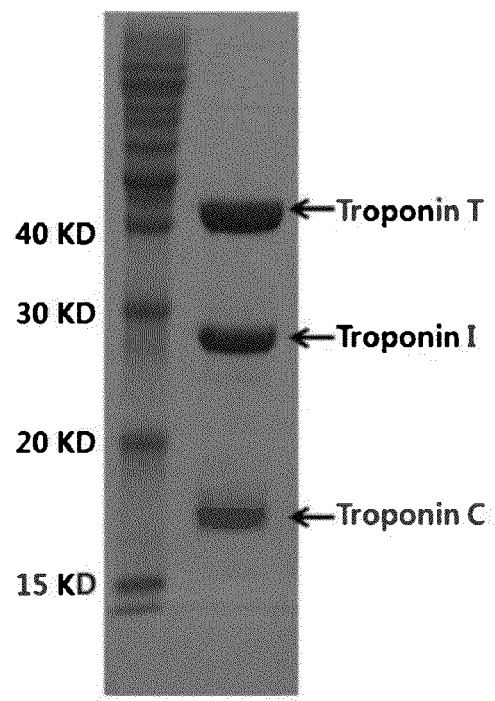
FIG. 4 shows the isolation of Troponin complex protein as purified by gel filtration.

In FIG. 4, a marker for indicating protein sizes was run on lane 1 and the fraction obtained from the above-mentioned purification processes was on lane 2.

EXAMPLE 6

Search for Aptamers of Troponin I by SELEX

<6-1> Construction of ssDNA (Single-Stranded DNA) Library

A library of 90 sequences, each having primer sequences for PCR amplification and cloning at opposite ends with a random DNA sequence of 40 bases between the primer sequences, was constructed (5'-CACCTAATACGACTCAC-TATAGCGGATCCGA-N40-CTGGCTCGAACAAGCT-TGC-3'; SEQ ID NO: 13).

In addition, a 5' primer (5'-CACCTAATACGACTCAC-TATAGCGGA-3'; SEQ ID NO: 14), a 3' primer (5'-GCAAGCTTGTTCGAGCCAG-3'; SEQ ID NO: 15) and a biotin-conjugated 3' primer (5'-Biotin-GCAAGCTTGTTC-GAGCCAG-3'; SEQ ID NO: 16) were used for PCR amplification and ssDNA production. All the oligonucleotides used in the present invention were synthesized and subjected to PAGE purification by Bionics (Korea).

<6-2> Immobilization of Human Cardiac Troponin I to Ni-NTA Magnetic Beads

The purified human cardiac Troponin I was immobilized to the magnetic bead Dynabead (Invitrogen, Norway), which allows the His-tag to bind to its cobalt-coated surface.

In this regard, the protein was fixed to the beads by washing 20 μL of the beads with a binding buffer (20 mM Tris, 300 mM NaCl, 3% glycerol, 0.01% Tween 20, 5 mM MgCl, pH 8.0) by means of an external magnet and incubating the beads with 150 μL of a binding buffer containing 150 pmol of the protein.

<6-3> Selection of Aptamer Specific for Human Cardiac Troponin I

To select aptamers specific for human cardiac troponin I, a specific separation method using a magnet was conducted.

First, a library of the ssDNAs (1 nmol) was dissolved in 100 μL of a binding buffer and was incubated at 90° C. for 3 min and then at 4° C. for one hour to allow the ssDNA to form the most stable conformation. Subsequently, this library was reacted for one hour with the Troponin I protein immobilized to the magnetic bead, with gentle agitation. Then, the beads were washed twice with the binding buffer to remove the ssDNA which remained unbound to the Troponin I immobilized to the beads.

Afterwards, the ssDNA was separated from the proteins bound thereto. In this context, the ssDNA and the proteins bound thereto were eluted with elution buffer (20 mM Tris, 300 mM NaCl, 3% glycerol, 0.01% Tween 20, 5 mM $MgCl_2$, 300 mM imidazole, pH8.0). The ssDNA eluate was precipitated in ethanol, dissolved in 100 μL of distilled water, and used as a template for PCR amplification using the 5' primer and the biotin-conjugated 3' primer in the presence of i-pfu polymerase (Intron Biotechnology, Korea). To isolate ssDNA for selection, the biotin-conjugated PCR product was incubated for one hour with streptavidin-coated magnetic beads in a coupling buffer (5 mM Tris-HCl, 5 mM EDTA, 1 M NaCl, 0.01%), followed by incubation with 100 μL of 100 mM NaOH for 5 min to separate only ssDNA. The ssDNA was obtained using an external magnet.

The first selected ssDNA was used in subsequent repetitive selection. For stringent selection, the amount of ssDNA and the concentration of Troponin I were gradually decreased in subsequent repetitions. During the selection process, the binding of ssDNA to Troponin I was monitored by measuring the concentration of the ssDNA eluted by the repeated selections with a UV spectrometer (Biochrom Libra S22 spectrometer). The results are shown in FIG. 5.

Figure 5:
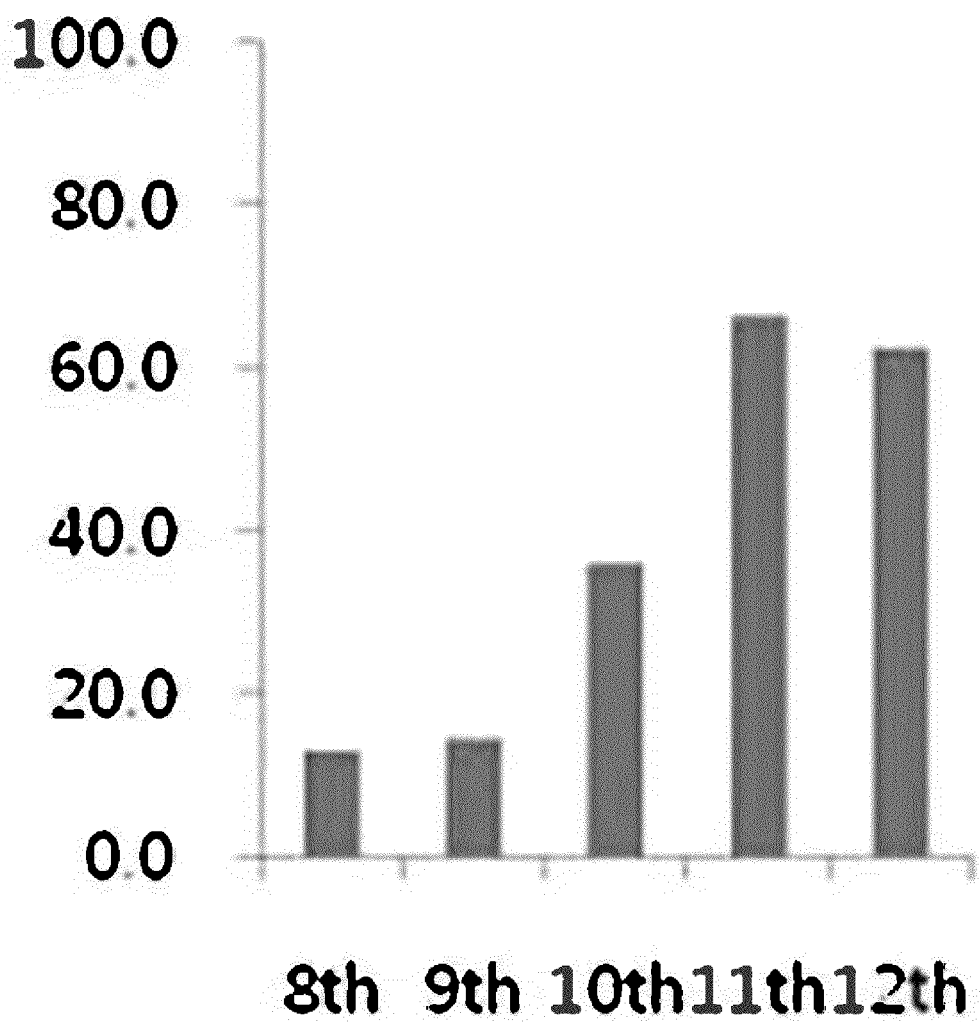
FIG. 5 is a graph showing the binding strength of ssDNA aptamers Troponin I as measured by a UV spectrometer according to selection of aptamer specific for Troponin I.

FIG. 5 shows the extent of binding of the aptamers with the protein that was immobilized to magnetic beads during the selection of the aptamers. The extent of binding is expressed as a percentage (%) of the concentration of the bound aptamer over the concentration of the aptamer used. As can be shown in FIG. 5, the numbers of the aptamer DNA binding to the protein increased with an increase in the selection round.

<6-4> Analysis of Sequence and Structure of Aptamers

The ssDNA selected in the $12^{th}$ round was amplified by PCR using the unmodified 5' and 3' primers and cloned to pENTR/TOPO (TOPO TA Cloning kit, Invitrogen, USA) which was then transformed into E. coli TOP10 (Invitrogen, USA). The clones harboring the ssDNA were purified using a miniprep kit (GeneAll, Korea) and subjected to base sequencing (COSMO Genetech, Korea). As a result, the ssDNA sequences were identified as SEQ ID NOS: 1 to 6 and are listed in Table 1, below.

Figure 6:
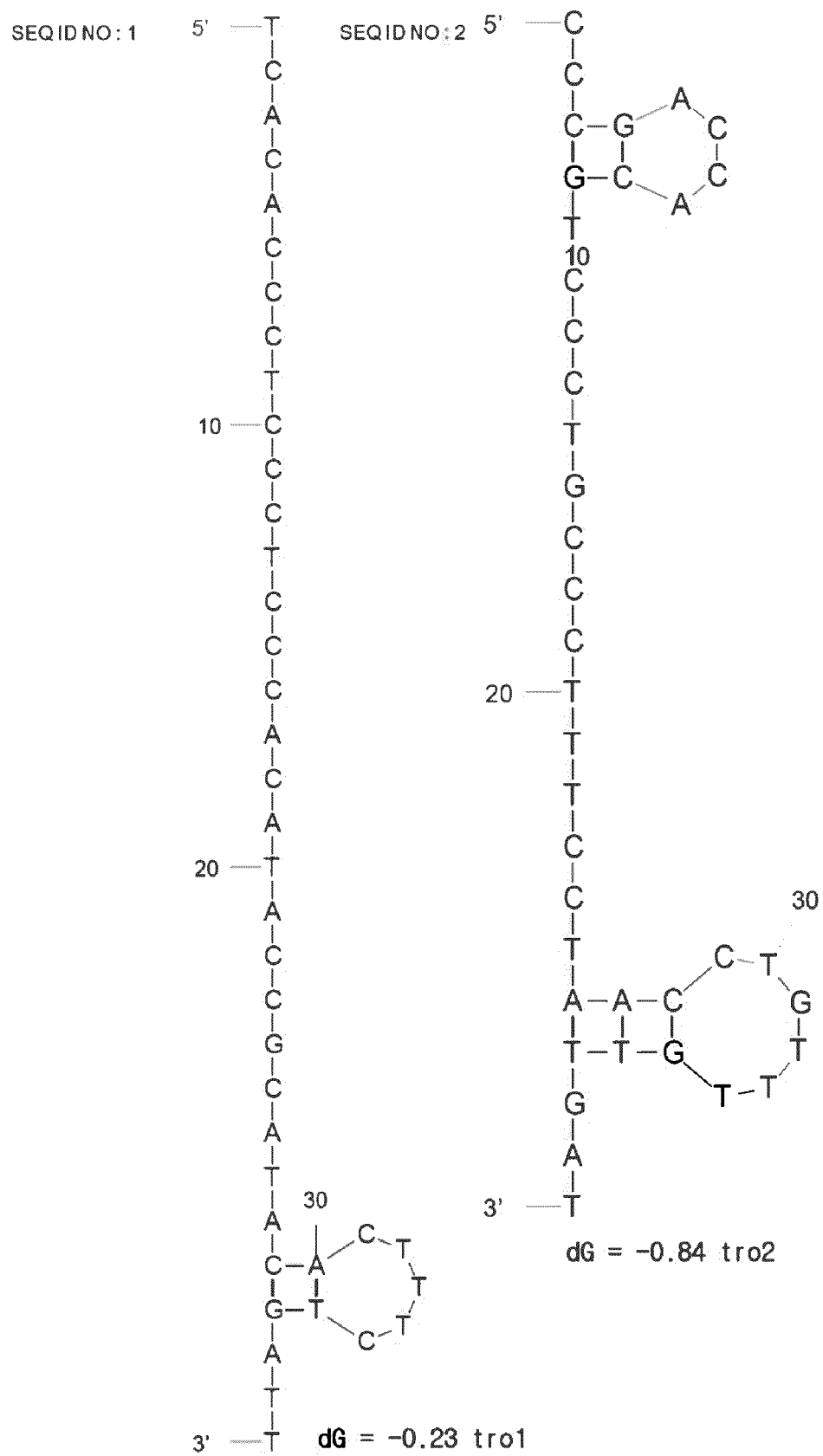
FIG. 6 shows secondary structures of the aptamers of SEQ ID NOS: 1 and 2 which specifically bind to human cardiac Troponin I.
Figure 7:
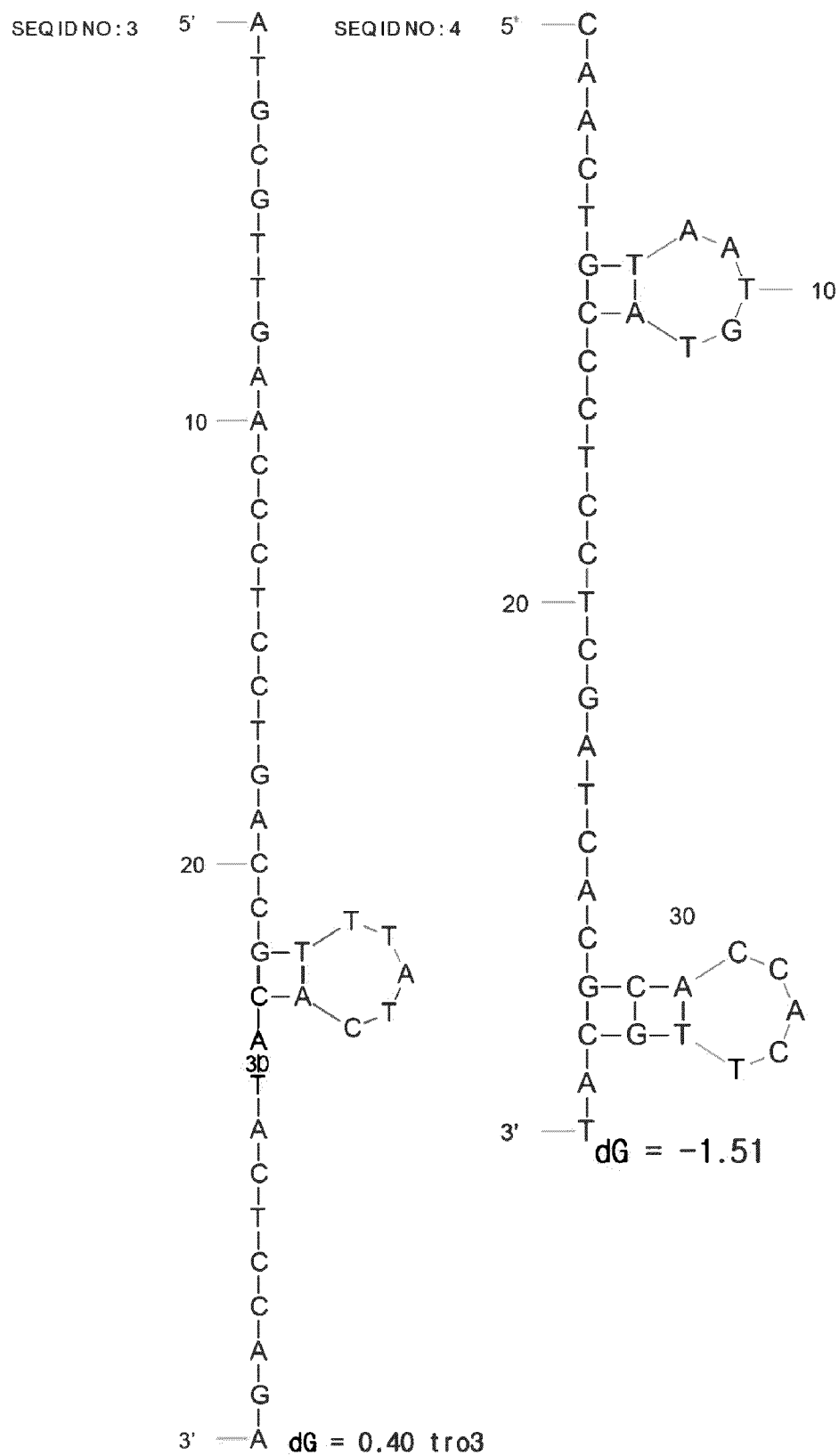
FIG. 7 shows secondary structures of the aptamers of SEQ ID NOS: 3 and 4 which specifically bind to human cardiac Troponin I.
Figure 8:
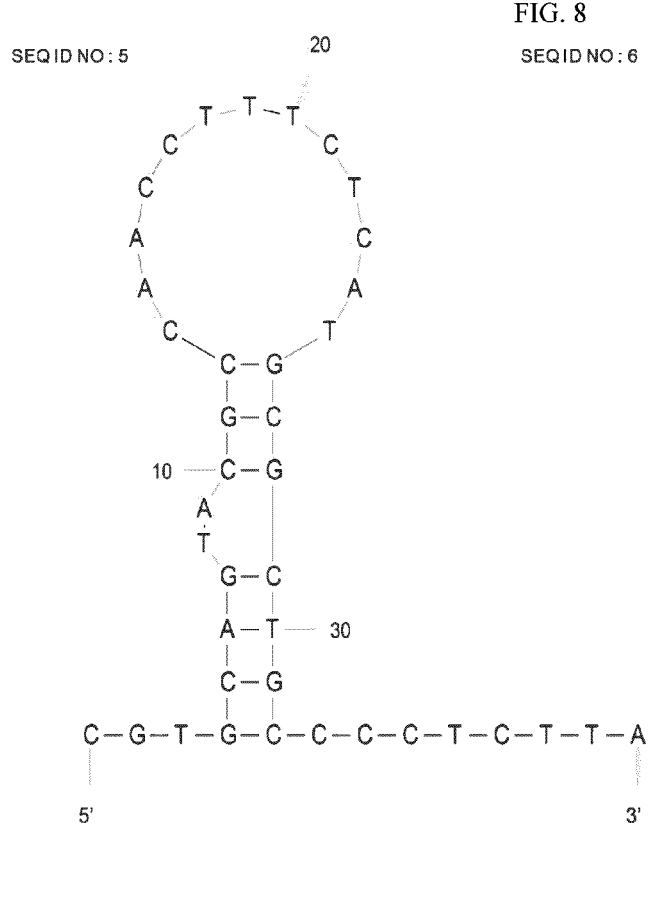
FIG. 8 shows secondary structures of the aptamers of SEQ ID NOS: 5 and 6 which specifically bind to human cardiac Troponin I.
Figure 9:
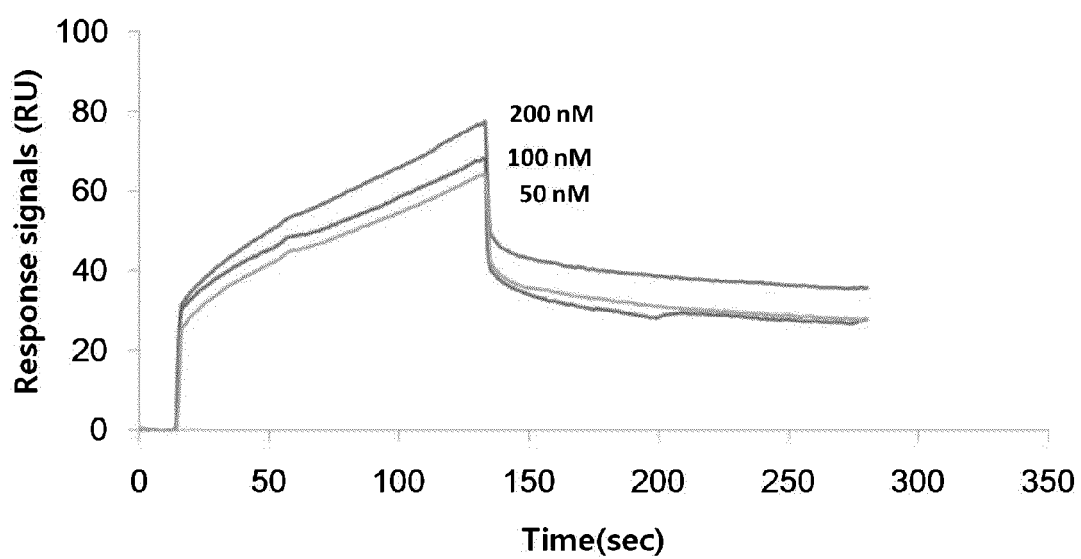
FIG. 9 is of SPR (surface Plasmon resonance) spectra showing the binding strength between Troponin I protein and the aptamer of SEQ ID NO: 1.
Figure 10:
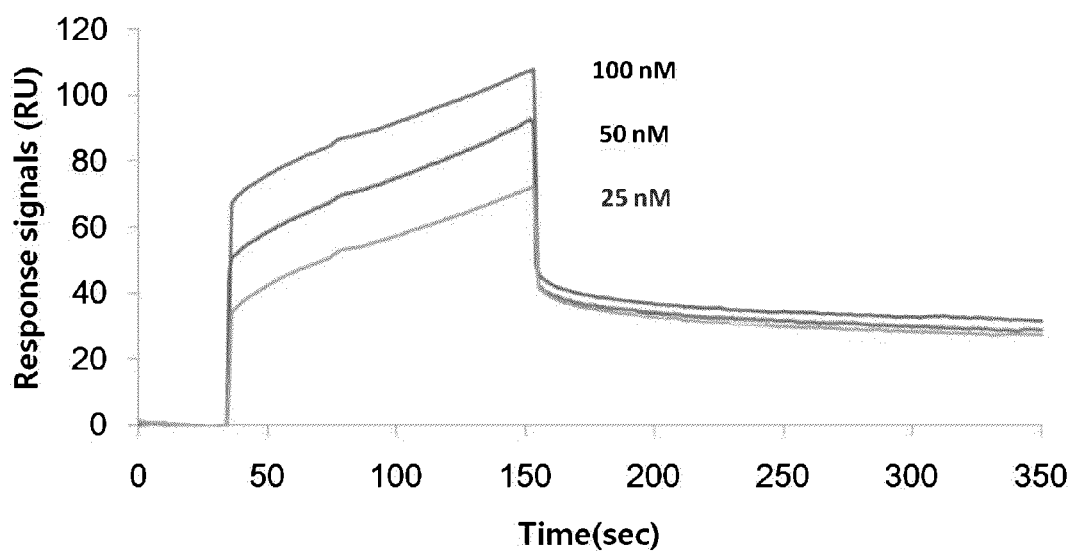
FIG. 10 is of SPR (surface Plasmon resonance) spectra showing the binding strength between Troponin I protein and the aptamer of SEQ ID NO: 2.
Figure 11:
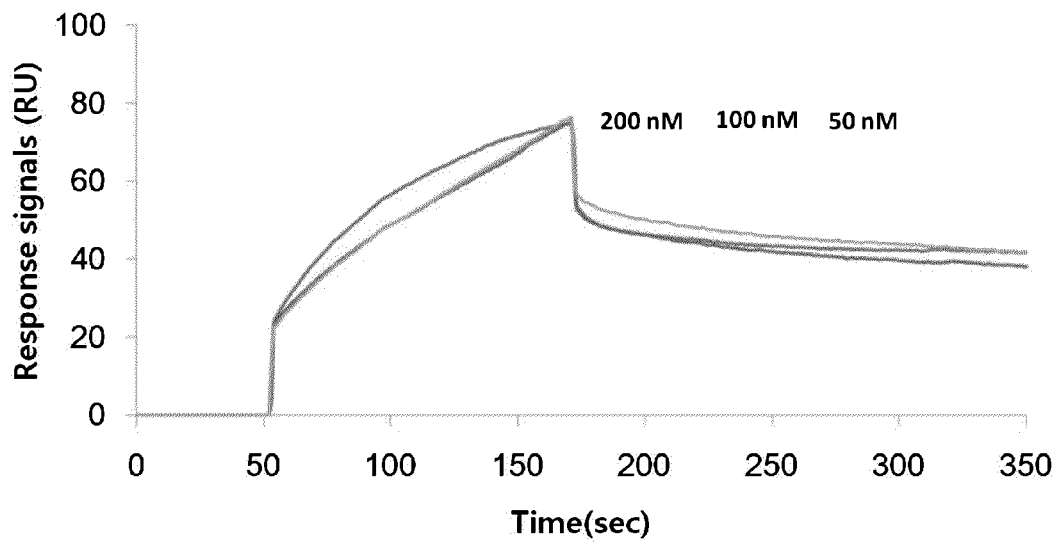
FIG. 11 is of SPR (surface Plasmon resonance) spectra showing the binding strength between Troponin I protein and the aptamer of SEQ ID NO: 3.
Figure 12:
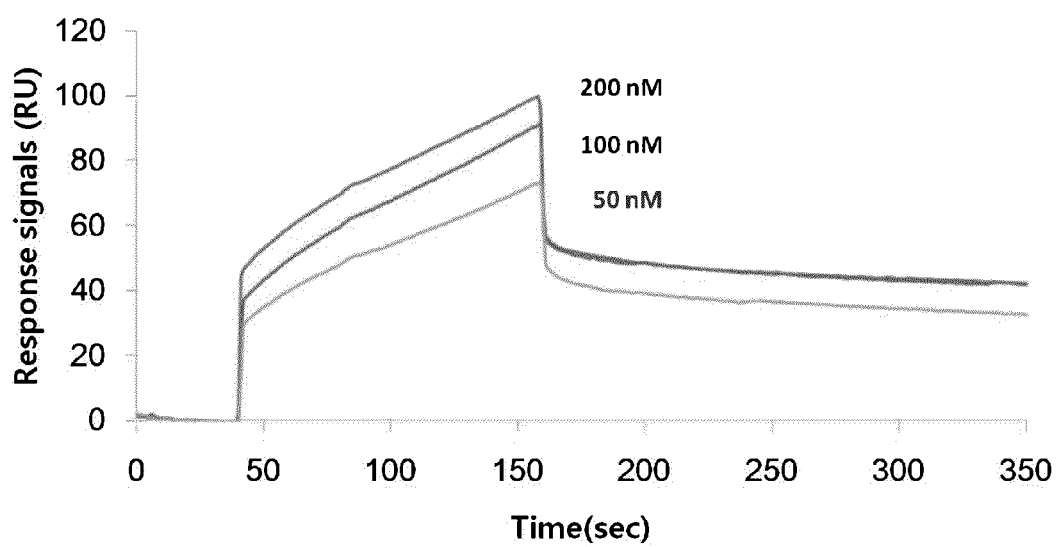
FIG. 12 is of SPR (surface Plasmon resonance) spectra showing the binding strength between Troponin I protein and the aptamer of SEQ ID NO: 4.
Figure 13:
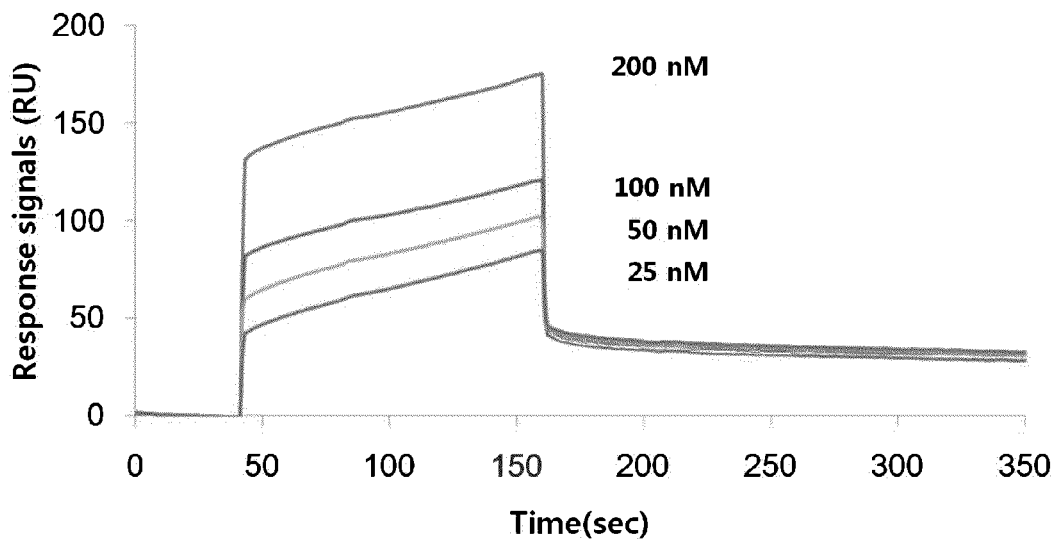
FIG. 13 is of SPR (surface Plasmon resonance) spectra showing the binding strength between Troponin I protein and the aptamer of SEQ ID NO: 5.
Figure 14:
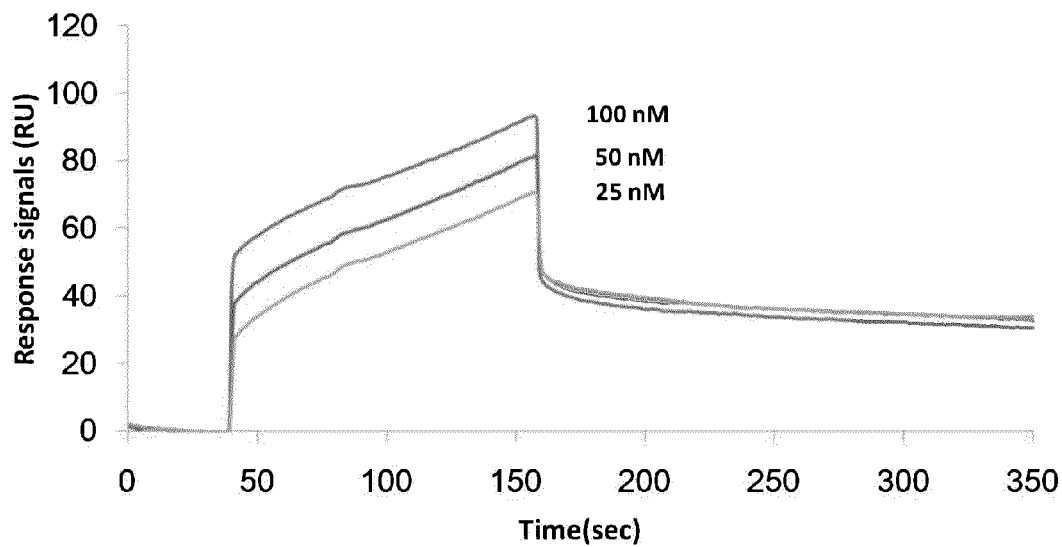
FIG. 14 is of SPR (surface Plasmon resonance) spectra showing the binding strength between Troponin I protein and the aptamer of SEQ ID NO: 6.
Figure 15:
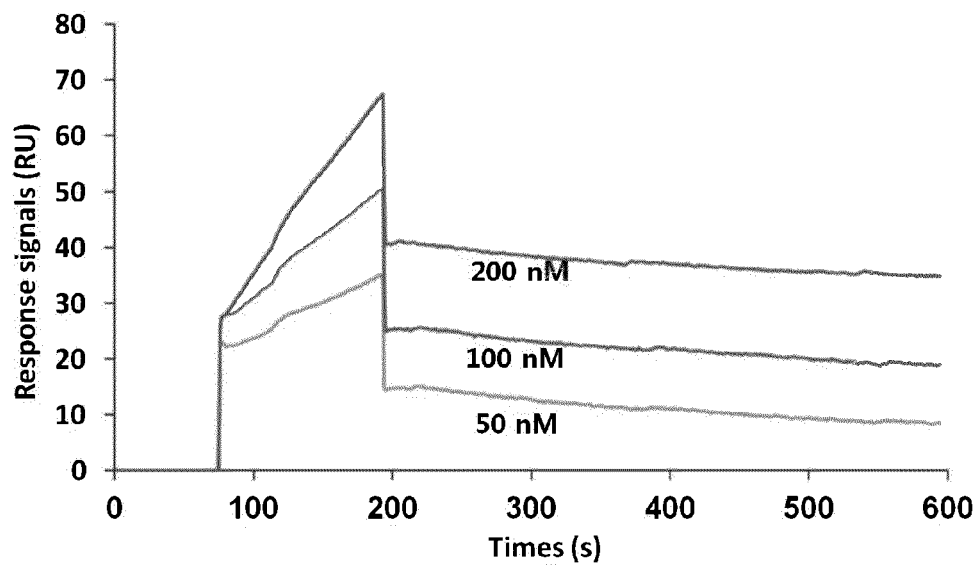
FIG. 15 is of SPR (surface Plasmon resonance) spectra showing the binding strength between Troponin I protein and an antibody.
Figure 16:
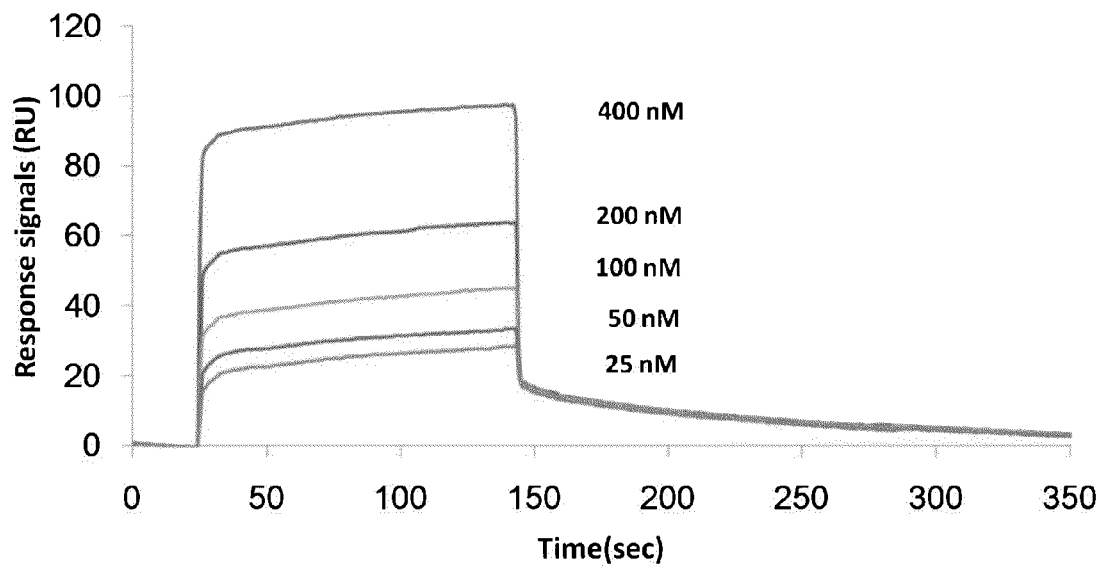
FIG. 16 is of SPR (surface Plasmon resonance) spectra showing the binding strength between Troponin complex protein and the aptamer of SEQ ID NO: 1.
Figure 17:
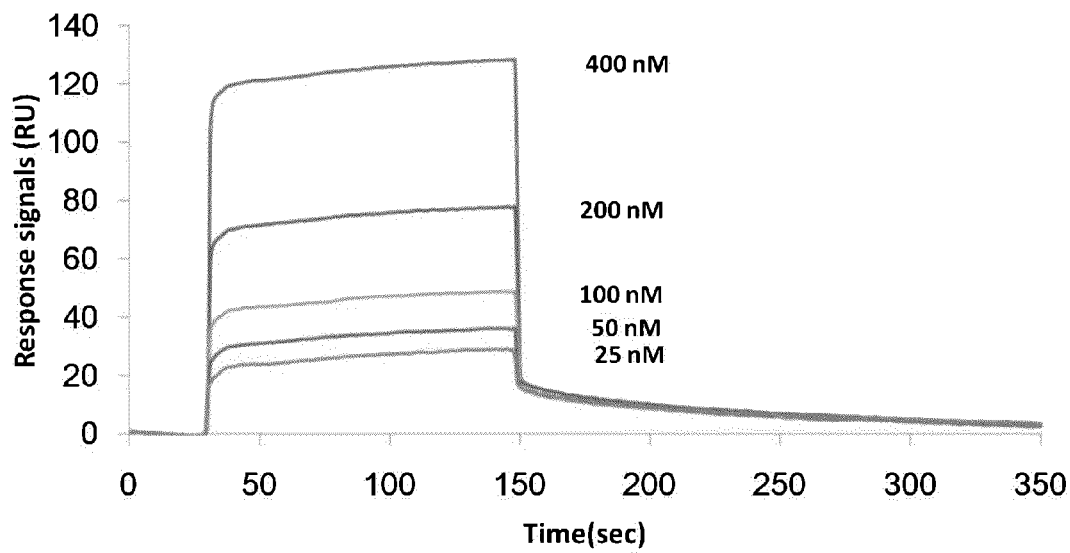
FIG. 17 is of SPR (surface Plasmon resonance) spectra showing the binding strength between Troponin complex protein and the aptamer of SEQ ID NO: 2.
Figure 18:
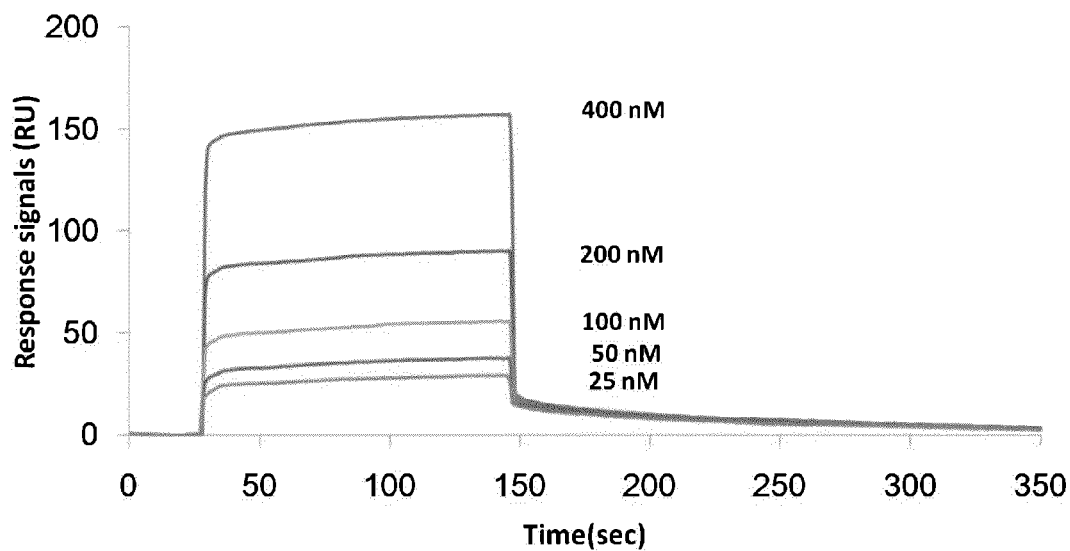
FIG. 18 is of SPR (surface Plasmon resonance) spectra showing the binding strength between Troponin complex protein and the aptamer of SEQ ID NO: 3.
Figure 19:
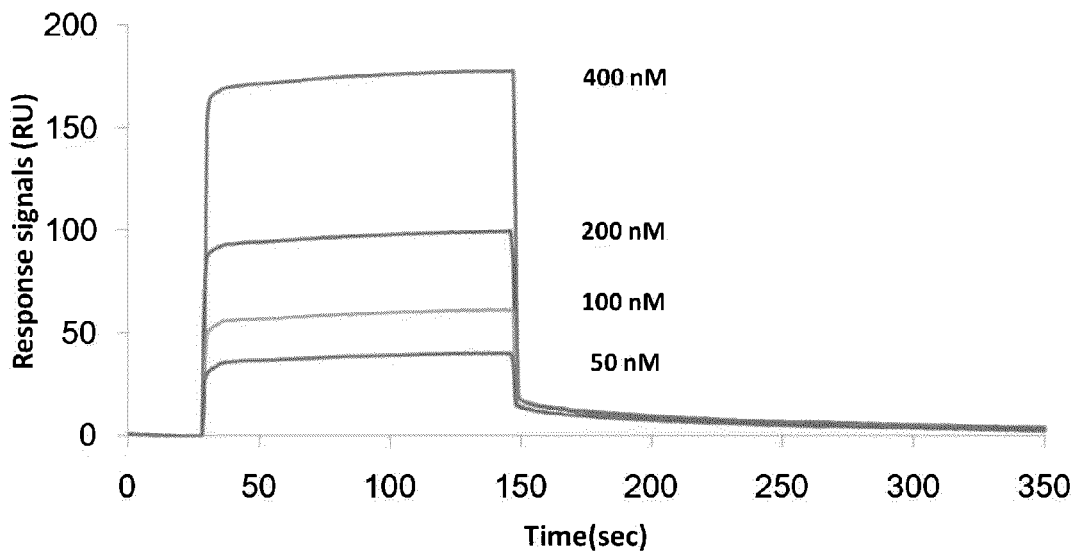
FIG. 19 is of SPR (surface Plasmon resonance) spectra showing the binding strength between Troponin complex protein and the aptamer of SEQ ID NO: 4.
Figure 20:
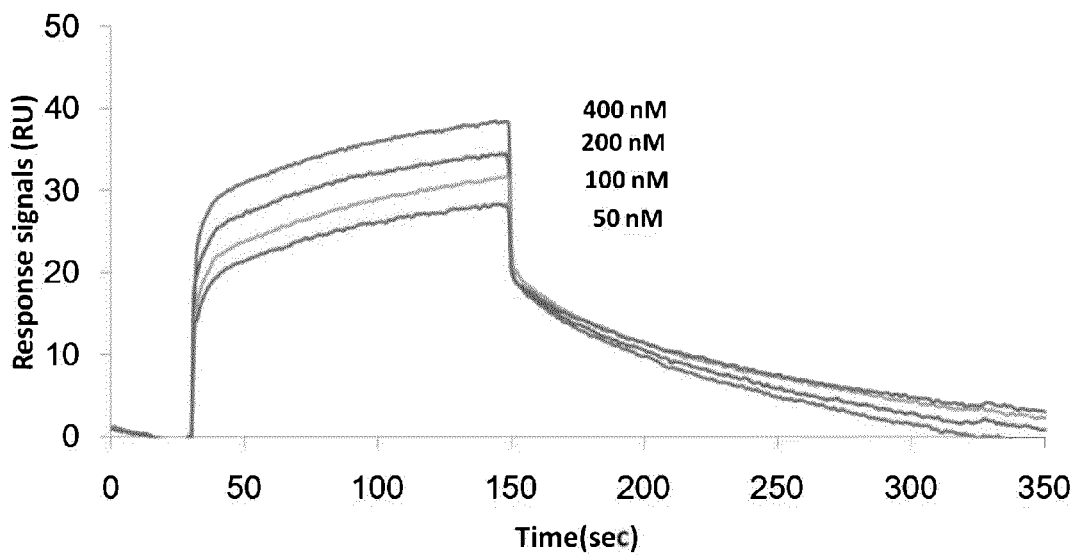
FIG. 20 is of SPR (surface Plasmon resonance) spectra showing the binding strength between Troponin complex protein and the aptamer of SEQ ID NO: 5.
Figure 21:
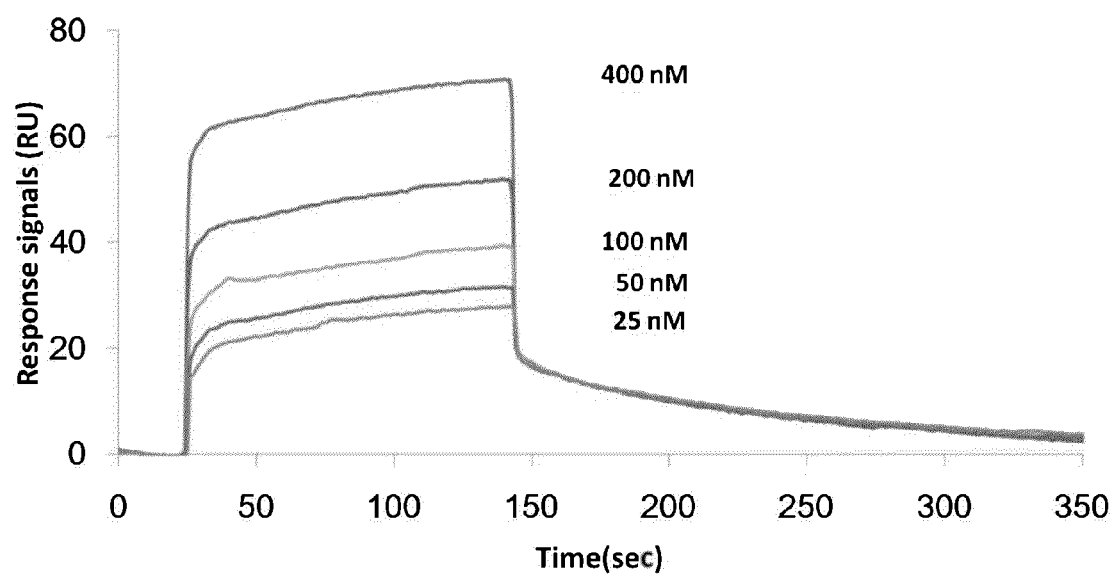
FIG. 21 is of SPR (surface Plasmon resonance) spectra showing the binding strength between Troponin complex protein and the aptamer of SEQ ID NO: 6.

To analyze the structural similarity of the selected ssDNA, the secondary structures of the selected ssDNA sequences were analyzed using the Mfold program (http://mfold.bioinfo.rpi.edu/cgi-bin/dna-form1.cgi). As shown in FIGS. 6 to 8, they were found to have a common stem-loop structure attributable to the consecutive T-C sequence.

TABLE 1

| SEQ ID NO: | Base Sequence |
| --- | --- |
| 1 | TCACACCCTCCCTCCCACATACCGCATACACTTTCTGATT |
| 2 | CCCGACCACGTCCCTGCCCTTTCCTAACCTGTTTGTTGAT |
| 3 | ATGCGTTGAACCCTCCTGACCGTTTATCACATACTCCAGA |
| 4 | CAACTGTAATGTACCCTCCTCGATCACGCACCACTTGCAT |
| 5 | CGTGCAGTACGCCAACCTTTCTCATGCGCTGCCCCTCTTA |
| 6 | CGCATGCCAAACGTTGCCTCATAGTTCCCTCCCCGTGTCC |

EXAMPLE 7

SPR (Surface Plasmon Resonance) Assay for Binding Strength between Troponin I and Aptamer SPR (surface Plasmon resonance) is a phenomenon occurring between light and electrons on metal such as gold in which when a light with a specific wavelength is incident on a metallic surface, most of the light energy is transferred to free electrons of the metal, resulting in resonance with the creation of evanescent wave. The binding strength can be determined by measuring the resonance wavelength shift dependent on a change in composition on the surface of the sample conjugated with the metal. To determine binding strength between Troponin I and the aptamers, SPR was measured using an Ni-NTA (Ni-Nitrilo-triacetic acid)-coated surface chip (Biacore AB, Sweden).

The Troponin I protein (200 nM) was immobilized to the Ni-NTA chip and then coupled with the aptamer DNAs. The aptamer DNAs were used at concentrations of 25 nM, 50 nM, 100 nM, and 200 nM. For comparison, the binding strength with cardiac Troponin I of a commercially available antibody (Abcam, U.K.) was also measured. Its Kd was observed to be 20.1 nM which is higher than that of the aptamers of the present invention.

SPR adsorption data and Kd values are shown in FIGS. 9 to 15 and Table 2, respectively.

TABLE 2

| Aptamer | Kd |
| --- | --- |
| SEQ ID NO: 1 | 3.41 nM |
| SEQ ID NO: 2 | 1.13 nM |
| SEQ ID NO: 3 | 1.14 nM |
| SEQ ID NO: 4 | 3.25 nM |
| SEQ ID NO: 5 | 270 pM |
| SEQ ID NO: 6 | 317 pM |
| Antibody (Comparative) | 20.1 nM |

The binding strength with troponin complex of aptamers was measured in the same way as above. The aptamer DNAs were used at concentrations of 50 nM, 100 nM, 200 nM and 400 nM. As a result, it was observed that troponin complex combined to troponin I effectively. Its Kd was observed which is higher than that of the binding troponin I or similar.

SPR adsorption data and Kd values are shown in FIGS. 16 to 21 and Table 3, respectively.

TABLE 3

| Aptamer | Kd |
| --- | --- |
| SEQ ID NO: 1 | 3.2 nM |
| SEQ ID NO: 2 | 4.5 nM |
| SEQ ID NO: 3 | 5.7 nM |
| SEQ ID NO: 4 | 10.6 nM |
| SEQ ID NO: 5 | 3.1 nM |
| SEQ ID NO: 6 | 3.4 nM |

It is understood to a person skilled in the art that the above description of the present invention is susceptible to various modifications, changes and adaptations, and the same are intended to be comprehended within the meaning and range of equivalents of the appended claims. Therefore, the embodiments and attached drawings disclosed in the present invention are not intended to limit the technical spirit of the present invention, but are intended to describe the invention. The technical spirit of the present invention is not limited to such embodiments and drawings.

What is claimed is:

1. A DNA aptamer specifically binding to human cardiac troponin I, wherein the DNA aptamer has a base sequence selected from the group consisting of SEQ ID NOS: 1 to 6.

2. A composition for diagnosis of an acute cardiovascular disease, comprising the DNA aptamer of claim 1.

3. A diagnostic kit for an acute cardiovascular disease, comprising the DNA aptamer of claim 1.

* * * * *

SEQUENCE LISTING

<160> NUMBER OF SEQ ID NOS: 16

<210> SEQ ID NO 1
<211> LENGTH: 40
<212> TYPE: DNA
<213> ORGANISM: Artificial Sequence
<220> FEATURE:
<223> OTHER INFORMATION: DNA specifically binding to human cardiac troponin I

<400> SEQUENCE: 1
tcacaccctc cctcccacat accgcataca ctttctgatt                               40

<210> SEQ ID NO 2
<211> LENGTH: 40
<212> TYPE: DNA
<213> ORGANISM: Artificial Sequence
<220> FEATURE:
<223> OTHER INFORMATION: DNA specifically binding to human cardiac troponin I

<400> SEQUENCE: 2
cccgaccacg tccctgccct ttcctaacct gtttgttgat                               40

<210> SEQ ID NO 3
<211> LENGTH: 40
<212> TYPE: DNA
<213> ORGANISM: Artificial Sequence
<220> FEATURE:
<223> OTHER INFORMATION: DNA specifically binding to human cardiac troponin I

<400> SEQUENCE: 3
atgcgttgaa ccctcctgac cgtttatcac atactccaga                               40

<210> SEQ ID NO 4
<211> LENGTH: 40
<212> TYPE: DNA
<213> ORGANISM: Artificial Sequence
<220> FEATURE:
<223> OTHER INFORMATION: DNA specifically binding to human cardiac troponin I

<400> SEQUENCE: 4
caactgtaat gtaccctcct cgatcacgca ccacttgcat                               40

<210> SEQ ID NO 5
<211> LENGTH: 40
<212> TYPE: DNA
<213> ORGANISM: Artificial Sequence
<220> FEATURE:
<223> OTHER INFORMATION: DNA specifically binding to human cardiac troponin I

<400> SEQUENCE: 5
cgtgcagtac gccaaccttt ctcatgcgct gcccctctta                               40

<210> SEQ ID NO 6
<211> LENGTH: 40
<212> TYPE: DNA
<213> ORGANISM: Artificial Sequence
<220> FEATURE:
<223> OTHER INFORMATION: DNA specifically binding to human cardiac troponin I

<400> SEQUENCE: 6

-continued

```
cgcatgccaa acgttgcctc atagttccct ccccgtgtcc                           40

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
ggatccatgg cggatgggag cag                                            23

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
aagctttcaa aactttttct tgcgg                                          25

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
gaattcatgt ctgacataga agaggtggtg                                     30

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ctcgagctat ttccagcgcc cggt                                           24

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
gaattcatgg atgacatcta caaggctgc                                      29

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ctcgagctac tccacaccct tcatgaactc                                     30

<210> SEQ ID NO 13
<211> LENGTH: 90
<212> TYPE: DNA
<213> ORGANISM: Artificial Sequence
<220> FEATURE:
```

```
<221> NAME/KEY: MISC_FEATURE
<222> LOCATION: (32)..(71)
<223> OTHER INFORMATION: n= a, t, g, or c
<220> FEATURE:
<223> OTHER INFORMATION: Primer

<400> SEQUENCE: 13
cacctaatac gactcactat agcggatccg annnnnnnnn nnnnnnnnnn nnnnnnnnnn      60
nnnnnnnnnn nctggctcga acaagcttgc                                      90

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
cacctaatac gactcactat agcgga                                          26

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
gcaagcttgt tcgagccag                                                  19

<210> SEQ ID NO 16
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)
<223> OTHER INFORMATION: n is biotin-conjugated g

<400> SEQUENCE: 16
ncaagcttgt tcgagccag                                                  19
```